United States Patent
Hirschmann, Jr. et al.

(10) Patent No.: US 9,498,382 B2
(45) Date of Patent: Nov. 22, 2016

(54) GREY COMPOUNDED INFRARED ABSORBING FACESHIELD

(71) Applicants: Jack Bouton Hirschmann, Jr., South Dartmouth, MA (US); Randell Bouton Hirschmann, South Dartmouth, MA (US)

(72) Inventors: Jack Bouton Hirschmann, Jr., South Dartmouth, MA (US); Randell Bouton Hirschmann, South Dartmouth, MA (US)

(73) Assignee: Oberon Company Div Paramount Corp., New Bedford, MA (US)

(*) Notice: Subject to any disclaimer, the term of this patent is extended or adjusted under 35 U.S.C. 154(b) by 0 days.

(21) Appl. No.: 14/525,881

(22) Filed: Oct. 28, 2014

(65) Prior Publication Data

US 2015/0113712 A1   Apr. 30, 2015

Related U.S. Application Data

(60) Provisional application No. 61/896,751, filed on Oct. 29, 2013.

(51) Int. Cl.

| | |
|---|---|
| *A41D 13/11* | (2006.01) |
| *A61F 9/06* | (2006.01) |
| *A42B 3/22* | (2006.01) |
| *G02B 5/28* | (2006.01) |
| *A41D 31/00* | (2006.01) |

(52) U.S. Cl.
CPC .............. *A61F 9/065* (2013.01); *A42B 3/225* (2013.01); *G02B 5/282* (2013.01)

(58) Field of Classification Search
CPC ................. B32B 17/10174; B32B 17/10513; B32B 2307/416; B32B 2307/418; B32B 2551/00; B32B 27/18; C08K 5/0041; C08K 3/22; C08K 13/02; C09D 5/32; B60R 1/088; G02B 5/22; G02B 5/223; G02B 1/11; G02B 5/02; G02B 1/04; G02B 1/14; G02B 2207/121; G02B 5/0841; G02B 5/282; G02B 5/287; G02B 5/204; A41D 13/11; A41D 13/1184; A41D 31/0022; A42B 3/225; A63B 2033/004; B29D 11/00634
See application file for complete search history.

(56) References Cited

U.S. PATENT DOCUMENTS

| | | | | |
|---|---|---|---|---|
| 4,707,383 A | * | 11/1987 | Mattes et al. ................. | 427/168 |
| 4,749,261 A | * | 6/1988 | McLaughlin et al. .......... | 349/16 |
| 4,935,166 A | * | 6/1990 | Lee et al. ...................... | 252/582 |
| 5,008,317 A | * | 4/1991 | Wolfer et al. ................. | 524/262 |

(Continued)

FOREIGN PATENT DOCUMENTS

WO   2010108975 A1   9/2010

OTHER PUBLICATIONS

Extended European Search Report and Written Opinion in EP15189837.6 dated Mar. 29, 2016.

*Primary Examiner* — Bobby Muromoto, Jr.
(74) *Attorney, Agent, or Firm* — Niro Law, Ltd.

(57) ABSTRACT

An improved personal protective eyewear device and composition has an arc flash faceshield to address issues regarding optical clarity, specifically full color acuity. The compound, which may be used with faceshields and similar PPE, provides a clear grey shield through the use of an infrared dye in that produces a true color lens. Unlike traditional green faceshields, the grey faceshield is a medium-density filter that allows 100% color acuity. The faceshield is preferably manufactured with polycarbonate material for high-impact and high-mass performance. Most preferably, the faceshield provides protection in the amount of 8.2 cal/cm2 or a category 2 arc hazard exposure protection.

2 Claims, 1 Drawing Sheet

(56) References Cited

U.S. PATENT DOCUMENTS

| | | | | |
|---|---|---|---|---|
| 5,223,334 | A * | 6/1993 | Green | 442/214 |
| 5,239,406 | A * | 8/1993 | Lynam | 359/275 |
| 5,359,174 | A * | 10/1994 | Smith et al. | 218/150 |
| 5,585,186 | A * | 12/1996 | Scholz et al. | 428/412 |
| 5,753,373 | A * | 5/1998 | Scholz et al. | 428/429 |
| 5,873,931 | A * | 2/1999 | Scholz et al. | 100/13 |
| 5,997,621 | A * | 12/1999 | Scholz et al. | 106/13 |
| 6,375,865 | B1 * | 4/2002 | Paulson et al. | 252/500 |
| 6,391,535 | B1 * | 5/2002 | Arimoto et al. | 430/619 |
| 6,417,619 | B1 * | 7/2002 | Yasunori et al. | 313/582 |
| 6,528,156 | B1 * | 3/2003 | Takizawa et al. | 428/323 |
| 6,597,525 | B2 * | 7/2003 | Kubota | 359/885 |
| 6,819,467 | B2 * | 11/2004 | Lynam | 359/275 |
| 6,965,191 | B2 * | 11/2005 | Koike et al. | 313/112 |
| 7,902,282 | B2 * | 3/2011 | Sato et al. | 524/399 |
| 7,982,380 | B2 * | 7/2011 | Kamiyama et al. | 313/111 |
| 8,144,399 | B2 * | 3/2012 | Steenblik et al. | 359/618 |
| 8,202,927 | B2 * | 6/2012 | Hiwatashi | 524/406 |
| 8,291,512 | B2 * | 10/2012 | Stoll | 2/15 |
| 2002/0012156 | A1 * | 1/2002 | Varaprasad et al. | 359/273 |
| 2002/0041424 | A1 * | 4/2002 | Lynam | 359/275 |
| 2002/0075580 | A1 * | 6/2002 | Kubota | 359/885 |
| 2002/0178491 | A1 * | 12/2002 | Yamamoto et al. | 2/428 |
| 2003/0054160 | A1 | 3/2003 | Fisher | |
| 2003/0156080 | A1 * | 8/2003 | Koike et al. | 345/60 |
| 2004/0025232 | A1 * | 2/2004 | Hartley et al. | 2/452 |
| 2004/0145802 | A1 * | 7/2004 | Miniutti et al. | 359/356 |
| 2006/0286381 | A1 * | 12/2006 | Naito et al. | 428/411.1 |
| 2007/0015094 | A1 * | 1/2007 | Habu | 430/348 |
| 2008/0102282 | A1 * | 5/2008 | Hu et al. | 428/412 |
| 2008/0167844 | A1 * | 7/2008 | Nasle et al. | 703/2 |
| 2009/0029135 | A1 * | 1/2009 | Sato et al. | 428/220 |
| 2009/0116132 | A1 * | 5/2009 | Hiwatashi et al. | 359/885 |
| 2009/0279168 | A1 * | 11/2009 | Hiwatashi et al. | 359/359 |
| 2010/0177397 | A1 * | 7/2010 | Kamiyama et al. | 359/609 |
| 2010/0210772 | A1 * | 8/2010 | Hiwatashi | 524/407 |
| 2010/0258752 | A1 * | 10/2010 | Mochizuki et al. | 250/515.1 |
| 2011/0043902 | A1 * | 2/2011 | Ishibashi et al. | 359/359 |
| 2011/0082246 | A1 * | 4/2011 | Sato et al. | 524/368 |
| 2012/0086909 | A1 | 4/2012 | Paulson | |
| 2012/0088106 | A1 * | 4/2012 | Jing et al. | 428/426 |
| 2012/0243077 | A1 * | 9/2012 | Osawa et al. | 359/356 |
| 2014/0256865 | A1 * | 9/2014 | Boulton et al. | 524/406 |

* cited by examiner

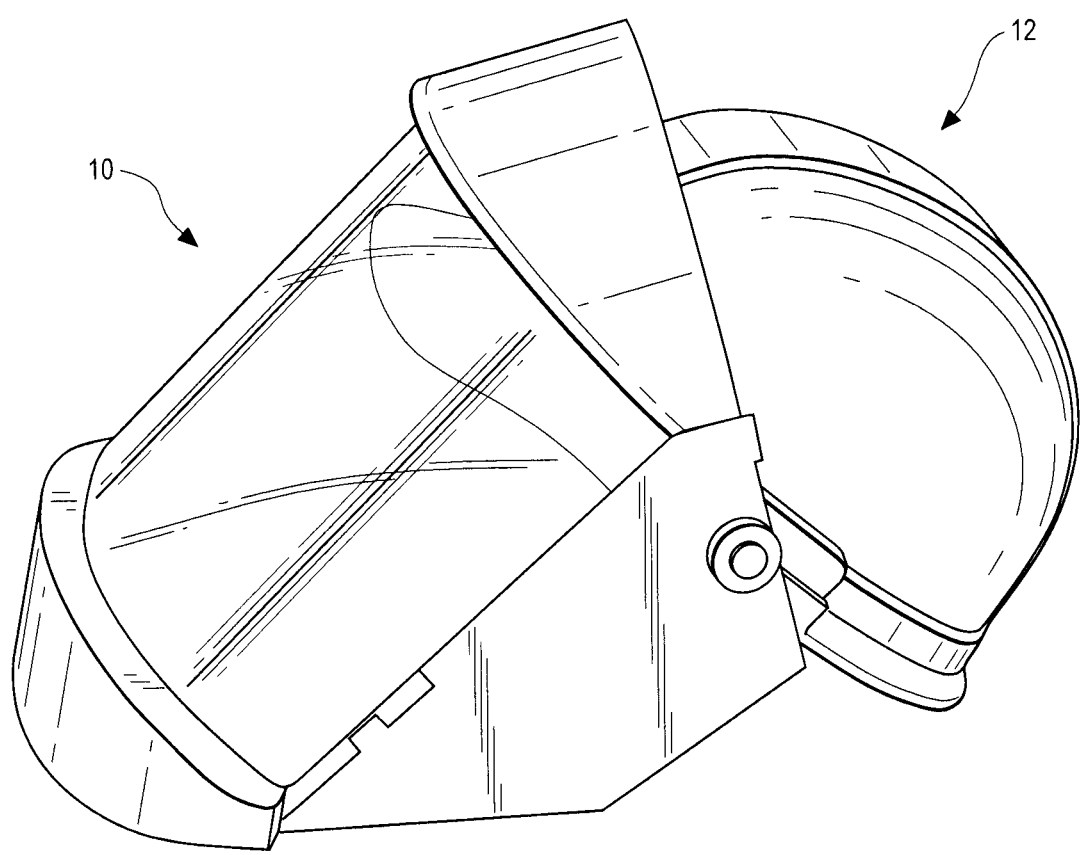

GREY COMPOUNDED INFRARED ABSORBING FACESHIELD

RELATED APPLICATION DATA

This application claims priority to provisional patent application No. 61/896,751, filed on Oct. 29, 2013.

FIELD OF INVENTION

The present invention relates to improved personal protective equipment for protecting electrical workers to flash-arc exposure. In particular, the present invention is directed towards an improved clear grey faceshield with a true clear color lens such that the user has full color acuity, thus, eliminating a key potential safety hazard in the presence of high voltage electrical equipment.

BACKGROUND OF THE INVENTION

When an electric current passes through air between ungrounded conductors, or between ungrounded conductors and grounded conductors, the temperatures can reach 35,000° F. Exposure to these extreme temperatures both burns the skin directly and causes ignition of clothing, which adds to the burn injury. The majority of hospital admissions due to electrical accidents are from arc-flash burns, not from shocks. Each year more than 2,000 people are admitted to burn centers with severe arc-flash burns. Arc-flashes can and do kill at distances of 10 ft (3 m).

Arc flash hazard exposure is a function of fault clearing time at an arcing current and a worker's distance from the event. Multiple techniques can be employed to limit risks related to such exposure. Arc flash injuries, for instance, are particularly prevalent among electricians. A myriad of solutions have been proposed to minimize such injuries.

One such method is through the use of Personal Protective Equipment (PPE) by line workers and others at risk, including protective hoods, suits, and eyewear. One of the common ways to prevent eye and face injuries from arcing is interposing a lens or semi opaque window between the wearer and the arcing source. One such problem with PPE, however, is the restrictions in movement and perception which they place upon such workers. In the case of protective eyewear, it may be essential for such workers to have full visual perception (including full color acuity) in order to perceive and operate upon the fault conditions which may be the cause of such arc flash conditions, as may be needed in the use of color coded electrical wiring and the like. As a result, there is a need for an arc flash PPE eyewear which provides optical clarity, and in particular full color acuity to the user.

DESCRIPTION OF THE PRIOR ART

One example of a prior art approach U.S. Pat. No. 6,375,865 to Paulson purports to disclose compositions that block electric-arc energy. Specifically, Paulson claims to disclose a composition and process for manufacturing electric-arc resistant objects that are at least partially transparent. As that patent defines the term, however "substantially transparent" means a composition which allows the passage of a sufficient amount of light to allow a person looking through the material to view objects under normal working conditions. It does not, however, teach or suggest color acuity for a user.

U.S. Pat. No. 3,382,183 to Donoian et. al. teaches a plastic optical filter related to the stabilization of infrared absorbing organic dyes in plastic substrates. A problem arises due to the degradation of the infrared dyes in sunlight and the fact that the Donoian device is simply an optical filter and not an arc shield.

A further approach is known to be offered through BSD Bildungs-und Servicezentrum GmbH (http://www.bsd-dresden.de/en). BSD has offered a Bayer Plastics product typically used in architectural or automotive applications to protect against sun light. BSD's product, however, is a faceshield with a laminant of protective film over the faceshield. As such, it is prone to degradation with prolonged use.

Still another publication is shown in U.S. Patent Application No. 2012/0086909 (Paulson), which discloses an arc shielding lens or a laminate for such a lens with a mixture of nanoparticles for thermal negation and absorption. However, nothing in this application teaches or suggests the need for color acuity to enable the wearer to better identify potential arc flash while still being protected from an arc flash occurrence.

In sum, the prior art fails to teach the use of a composition for a PPE faceshield which enables full color acuity by a wearer during use.

DEFINITION OF TERMS

The following terms are used in the claims of the patent as filed and are intended to have their broadest plain and ordinary meaning consistent with the requirements of the law.

"Color acuity" means the ability to discern and distinguish between colors in the visible light spectrum.

Where alternative meanings are possible, the broadest meaning is intended. All words used in the claims set forth below are intended to be used in the normal, customary usage of grammar and the English language.

OBJECTS AND SUMMARY OF THE INVENTION

The apparatus and method of the present invention generally includes a faceshield for blocking or absorbing thermal infrared energy incident to an arc flash incident. The faceshield is comprised of an infrared dye mixed with a substrate material for providing a gray lens or shield which permits full color acuity. The faceshield further includes a frame or similar support structure for the lens comprised of polycarbonate or similar non-conductive material.

The immediate application of a present invention will be seen in providing personal protective equipment for electrical workers exposed to arc flash conditions whereby the workers have full color acuity to recognize wire coloring.

Thus can be seen that one object of the present invention is to provide a faceshield for preventing injury due to infrared thermal energy due to arc flash events.

A further object of the present invention is to provide a faceshield which inhibits the tinting or discoloration of objects being viewed therethrough.

Still another object of the present invention is to provide a faceshield which can dissipate up to 8 cal/cm$^2$ of thermal energy incident to an arc flash event.

Yet another object of the present invention is to provide a faceshield which includes a tint for blocking infrared thermal energy.

Still another object of the present invention is to provide a faceshield which provides an electrical worker protection from arc flash events combined with a superior ability to detect and treat arc flash conditions over prior faceshield compositions.

It should be noted that not every embodiment of the claimed invention will accomplish each of the objects of the invention set forth above. In addition, further objects of the invention will become apparent based the summary of the invention, the detailed description of preferred embodiments, and as illustrated in the accompanying drawings. Such objects, features, and advantages of the present invention will become more apparent in light of the following detailed description of a best mode embodiment thereof, and as illustrated in the accompanying drawings.

BRIEF DESCRIPTION OF THE DRAWINGS

FIG. 1 shows a perspective view of a faceshield according to a first preferred embodiment of the invention.

DETAILED DESCRIPTION OF THE INVENTION

Set forth below is a description of what is currently believed to be the preferred embodiment or best examples of the invention claimed. Future and present alternatives and modifications to this preferred embodiment are contemplated. Any alternatives or modifications which make insubstantial changes in function, in purpose, in structure or in result are intended to be covered by the claims in this patent.

FIG. 1 shows a first preferred embodiment of a faceshield 10 constructed in accordance with the present invention. The faceshield 10 is attached to a hard hat 12 or other type of headgear and protects users from electric arcs while at the same time allowing the user to view objects without any alteration to the color of such objects. The substrate for this product is preferably an acrylic, but may also include acrylics, propionates, acetates, butyrate and polycarbonate or similarly clear plastics known to those of skill in the art.

In order to provide the necessary user protection for the optically clear face shield 10 of the present invention, the invention should further include a tin oxide particulate for blocking infrared thermal energy associated with arc flashes and similar events. Such particulate is not of a nanoparticle size. Rather, such a particle for use with the present invention is a typically very small cube of tin oxide in a range of 5-15 microns, and most preferably about 10 microns. However, simply adding tin oxide to an optically neutral substrate will not provide an even distribution of the tin oxide throughout the substrate.

Because of its size, a coating on each particle is important for it to disperse uniformly in the plastic, such coating being applied by fluidized bed, sol-gel, sputtering and evaporation known to those of skill in the art. Without the coating, the particles will clump together and not disperse evenly in the processing of the particles in mixing with the optically clear plastic substrate and the molding of the plastic part. In the absence of such a coating, the faceshield will have a haze that will affect the visibility of the optical part (shield or lens) and prevent the color acuity provided by the present invention.

The above description is not intended to limit the meaning of the words used in the following claims that define the invention. Rather, it is contemplated that future modifications in structure, function or result will exist that are not substantial changes and that all such insubstantial changes in what is claimed are intended to be covered by the claims. For instance, those of skill will understand that the instance invention can also apply to other forms eyewear beside faceshields. Likewise, it will be appreciated by those skilled in the art that various changes, additions, omissions, and modifications can be made to the illustrated embodiments without departing from the spirit of the present invention. All such modifications and changes are intended to be covered by the following claims.

We claim:

1. A faceshield assembly for blocking thermal infrared energy, the faceshield assembly comprising:
   a protective headgear;
   a polycarbonate frame, and
   a lens providing full color acuity within the visible light spectrum, the lens compromised of a dye that blocks infrared waves and a substrate material, the substrate material and first dye being chosen and blended in proportion so that faceshield will block at least up to 8 cal/cm$^2$ thermal energy, the lens further comprising:
   a) a substrate consisting of an optically clear plastic selected from the group consisting of polycarbonate, acrylic, propionate, acetate, butyrate and polycarbonate; and
   b) a tin oxide particulate dispersed substantially uniformly as coated particles within said substrate.

2. The faceshield assembly of claim 1, wherein the tin oxide particulate has a size range of about 5 to 15 microns per particle.

\* \* \* \* \*